United States Patent [19]
Lewis et al.

[11] Patent Number: 5,746,768
[45] Date of Patent: May 5, 1998

[54] SCISSOR ACTION LOW PROFILE SURGICAL HAND INSTRUMENT

[75] Inventors: Ralph Lewis, Basking Ridge, N.J.; Troy Hershberger, Warsaw, Ind.

[73] Assignee: Biomet, Inc., Warsaw, Ind.

[21] Appl. No.: 591,150

[22] Filed: Jan. 25, 1996

[51] Int. Cl.⁶ ................................................. A61B 17/00
[52] U.S. Cl. ........................................................ 606/205
[58] Field of Search .............................. 606/1, 174, 51, 606/52, 205–211; 128/750–755; 294/99.2

[56] References Cited

U.S. PATENT DOCUMENTS

| | | |
|---|---|---|
| 284,216 | 6/1883 | Dyson-Hughes . |
| 291,729 | 9/1884 | Greig . |
| 331,109 | 11/1885 | McWhinney et al. . |
| 620,853 | 3/1899 | Richter . |
| 931,317 | 8/1909 | Kjellerstedt . |
| 1,002,961 | 9/1911 | Beuoy et al. . |
| 1,079,128 | 11/1913 | Howe . |
| 1,359,164 | 11/1920 | Giudice . |
| 1,513,367 | 10/1924 | Brix . |
| 1,832,879 | 11/1931 | Ruskin . |
| 2,109,147 | 2/1938 | Grosso . |
| 2,876,778 | 3/1959 | Kees, Jr. .................. 606/208 |
| 3,557,792 | 1/1971 | Rubin . |
| 3,921,641 | 11/1975 | Hulka . |
| 4,088,134 | 5/1978 | Mazzariello . |
| 5,122,130 | 6/1992 | Keller . |

FOREIGN PATENT DOCUMENTS

| | | |
|---|---|---|
| 0134235 | 6/1887 | France . |
| 106567 | 11/1889 | Germany . |
| 2144041 | 9/1971 | Germany . |

OTHER PUBLICATIONS

Figs. 1–15; Apioues, Etc.; Jun. 1887; One page of drawings.

*Primary Examiner*—William Lewis
*Attorney, Agent, or Firm*—Liell & McNeil

[57] ABSTRACT

A scissor action low profile hand instrument includes a first member pivotably attached to a second member at a pivot point. The instrument has a surgical tip separated from a handle by a middle section. A centerline passing through the pivot point separates each half of the handle and each half of the surgical tip. The middle section of the instrument includes switchback segments that are positioned on opposite sides of the centerline. The switchback segments allow the instrument to retain a relatively small maximum width over a large portion of its middle section when moved from a closed position to a spread position.

14 Claims, 7 Drawing Sheets

SCISSOR ACTION LOW PROFILE SURGICAL HAND INSTRUMENT

FIELD OF THE INVENTION

The present invention relates generally to surgical hand instruments, and more particularly to scissor action surgical hand instruments having a low profile cross section along an extended portion of its midsection.

BACKGROUND OF THE INVENTION

In the past, most major surgical procedures developed using relatively invasive or open techniques. For example, chest surgery could involve cutting open the patient's chest and spreading the patient's ribs in order to gain easy access and a clear view to whatever organ was undergoing surgical repair. Over time, a wide variety of scissor action surgical hand instruments have developed for use with these open surgical procedures. These instruments include a wide variety of forceps, clamps, cutting instruments, etc. in a wide range of lengths, various curvatures, and a myriad of differently shaped surgical working tips. Examples of such prior art instruments are illustrated in the 5th edition Surgical Instrument Catalog of Walter Lorenz Surgical Inc.

These prior art scissor action hand instruments for open surgery carry several features in common. Each instrument typically includes first and second metallic members pivotably attached to one another in their middle portions with a pin. Each instrument includes a surgical tip separated from a handle portion by a middle section. The surgical tip is worked by pivoting the handle portions toward and away from one another about the pivot point with scissor action hand movement. The design of these instruments is rarely if ever concerned with the profile cross section of the instrument along its midsection since the open surgical techniques put little or no constraints on the shape or configuration of the middle section of these prior art instruments. While most of these prior art instruments have a low profile when in a closed position, the width of the instrument when pivoted to a spread position increases significantly. The relatively large profile width of these instruments over their midsection when spread open renders them unsuitable for many of today's less invasive surgical techniques.

The surgical trend of today is to convert the open surgical techniques of the past into less invasive methods in which the surgeon enters the patient's body through small incisions. Instead of opening the patient's chest, the surgeon might insert a surgical camera through one small incision and a variety of surgical instruments through other relatively small incisions at particular locations around the patient's body, depending upon the particular surgical site needing attention. A surgeon typically views the area undergoing surgery on a video screen while manipulating the surgical tips of instruments in the surgical area from the handle portions of the instruments, which are protruding out of the patient. Because of the relatively small incision sizes and other obstacles, such as ribs, many of the open surgical instruments of the prior art cannot be utilized because the instruments often cannot be adequately spread open without impinging on an obstacle or enlarging the incision opening. In response, a wide variety of different surgical instruments have developed that include an extended low profile middle section that renders them suitable for use in the less invasive surgical techniques. One example of such a type of low profile instrument might be rotary action forceps that are intended as a substitute for the scissor action forceps used in the past in an equivalent open surgical procedure.

Examples of such rotary action instruments include those described in U.S. Pat. No. 4,088,134 and 3,291,641 to Mazzariello and Hulka, respectively. Both of these prior art designs use a tube and shaft mechanism to open and close forcep jaws on the distal end. The shortcomings of rotary forceps begin with the fact that the tissue to be grasped much be approached from the side, and the hand motion is different from familiar scissor action instruments. This means that the incision into the patient must be placed away from the most desirable location, and forces the surgeon to use unfamiliar hand movements. The side approach required by these instruments also renders it more difficult to maintain a particular focal point at the end of the forceps.

Because most surgeons have developed their own field and technique in an open surgical setting, they are often reluctant to adopt less invasive surgical techniques because the switch involves such a profound change. In switching to a less invasive technique, the surgeon can no longer have direct view of the area undergoing surgery and must also typically adopt many unfamiliar low profile surgical instruments. For instance, the surgeon might necessarily need to use an unfamiliar rotary action set of forceps having an unfamiliar action, weight, balance, relative motion ratio and tactile shape. The scissor action forceps for open surgery that they have been accustomed to using are completely different. Thus, a switch to the less invasive surgical techniques of today have not been as forthcoming as desired. The profound differences between open surgical techniques and less invasive surgical techniques can be attributed at least in part to the requirement of the surgeon to use different instruments. If the surgeon opts to use familiar scissor action instruments for open surgery in a less invasive technique, a wide variety of lengths would be required in order to reach a range of depths into the patient. Mazzariello recognized that the instruments for open surgery have the limitation that unless the incision opening is very close to the pivot, the incision will be enlarged by the spreading movement of the instrument.

The present invention is intended to overcome these and other problems associated with adopting less invasive surgical techniques.

SUMMARY OF THE INVENTION

In responding to these problems, the present invention provides a scissor action low profile surgical hand instrument having a first member pivotably attached to a second member. Each member has a handle portion separated from a surgical tip by a middle portion. The members are pivotably attached in their middle portions. A centerline passing through the pivot point separates the handle portions and the surgical tip portions from one another. The middle portion of the first member includes at least one switchback segment that is positioned at least partially on an opposite side of the centerline from one of either the handle portion or the surgical tip portion. The second member likewise has at least one switchback segment in its middle portion positioned at least partially on an opposite side of the centerline from one of either its handle portion or surgical tip portion. The switchback segment on the second member is located adjacent the switchback segment of the first member. Finally, the instrument has a spread position with a maximum width over a midsection of its length substantially smaller than a maximum width over an equivalent midsection of a corresponding scissor action hand instrument for open surgery.

In another embodiment of the invention, a scissor action low profile surgical hand instrument includes a first member pivotably attached to a second member at a pivot point located in the middle portions of the members. A centerline passes through the pivot point and separates the handle portions and the surgical tip portions from one another. The first member has a distal switchback segment positioned distally of the pivot point and at least partially on an opposite side of the centerline from the surgical tip portion of the first member. The second member has a distal switchback segment positioned at least partially on an opposite side of the centerline from the surgical tip portion of the second member and at a location adjacent the distal switchback segment of the first member. The instrument has a closed maximum width in the middle portions of the members when in a closed position that is about the same as a spread maximum width of the same middle portions when the instrument is in a spread position.

One object of the present invention is to ease the transition of surgeons from open surgical techniques to less invasive surgical techniques.

Another object of the present invention is to provide scissor action surgical hand instruments with a low profile cross section over a substantial portion of its midsection.

Still another object of the present invention is to provide low profile surgical hand instruments with a feel and function similar to corresponding scissor action surgical hand instruments for open surgery.

Another object of the present invention is to provide low profile scissor action surgical hand instruments with a maximum width over its midsection that remains substantially unchanged when the instrument is spread open.

DETAILED DESCRIPTION OF THE PREFERRED EMBODIMENTS

Figure 1:
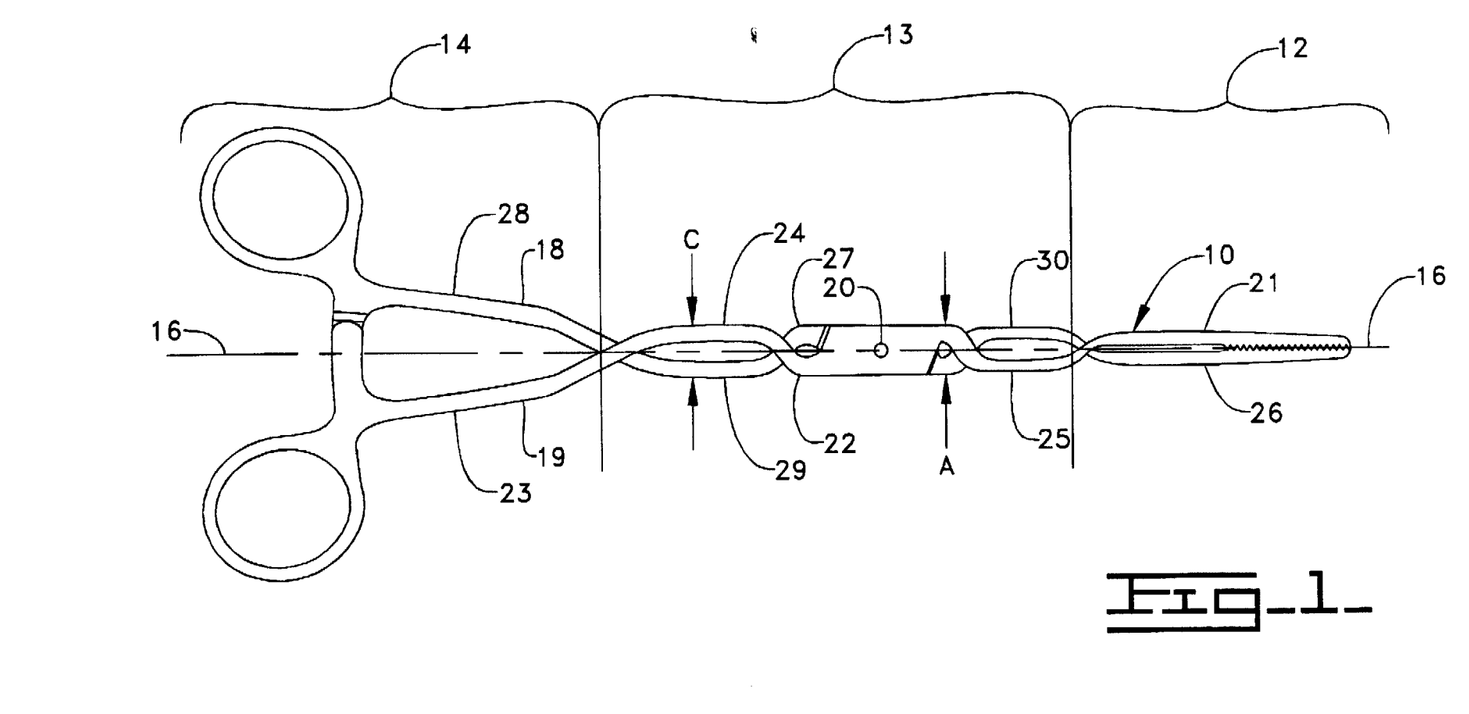
FIG. 1 is a front elevational view of a low profile surgical hand instrument according to one embodiment of the present invention in a closed position.

Referring now to FIG. 1, a scissor action low profile surgical hand instrument 10 includes a surgical tip 12 separated from a handle 14 by a middle section 13. In this example embodiment, instrument 10 is a pair of Foerster sponge forceps. Like corresponding instruments of the prior art, instrument 10 consists essentially of a first member 18 and second member 19, each of which is formed from a single solid piece of a suitable surgical metallic alloy. First member 18 includes a handle portion 28 separated from a surgical tip portion 26 by a middle portion 27. Middle portion 27 corresponds substantially in length to the middle section 13 of the overall instrument. The second member 18 likewise includes a handle portion 23 separated from a surgical tip portion 21 by a middle portion 22. First member 18 and second member 19 are pivotably pinned to one another in their respective middle sections 27 and 22 at a pivot point 20. A centerline 16 passes through pivot point 20 and separates handle portion 28 from handle portion 23 as well as surgical tip portion 21 from surgical tip portion 26.

First member 18 includes a distal switchback segment 30 in middle portion 27 between pivot point 20 and surgical tip portion 26. Segment 30 is positioned on an opposite side of centerline 16 from surgical tip portion 26. Second member 19 also includes a distal switchback segment 25 in its middle portion 22 that is located between pivot point 20 and surgical tip portion 21 and adjacent distal switchback segment 30. Distal switchback segment 25 is positioned on an opposite side of centerline 16 from surgical tip portion 21. First member 18 also includes a proximal switchback segment 29 located between handle portion 28 and pivot point 20. Proximal switchback segment 29 is also located on an opposite side of centerline 16 from handle portion 28. Finally, the second member 19 includes a proximal switchback segment 24 located on an opposite side of centerline 16 from handle portion 23. In order to gain the low profile characteristics of the present invention, each pair of switchback segment pairs 24/29 and 30/25 are located adjacent one another as shown.

Figure 2:
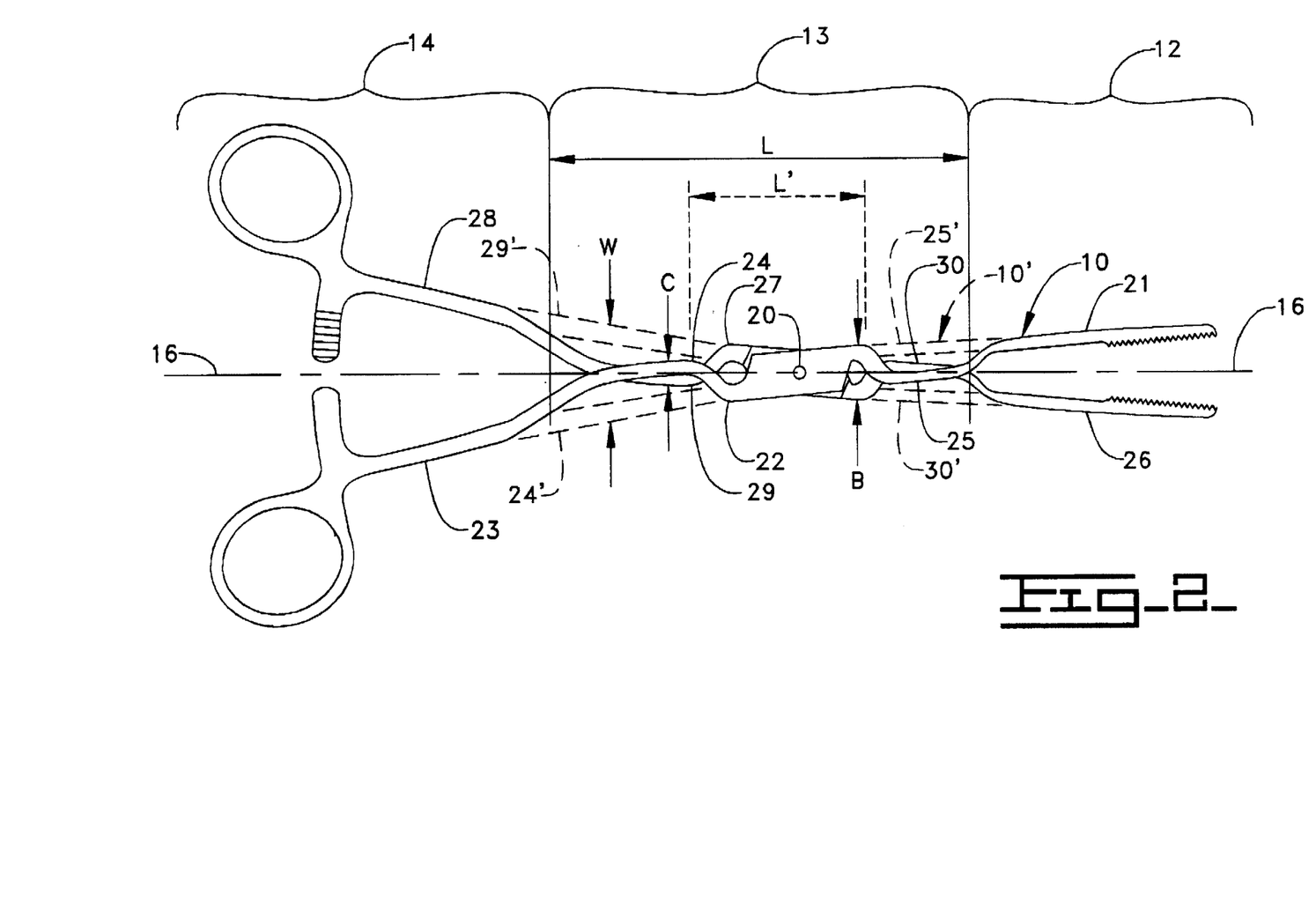
FIG. 2 is a front elevational view of the low profile surgical hand instrument of FIG. 1 shown in a spread position.

Referring now to FIG. 2, instrument 10 is shown in a spread position with the two members pivoted away from one another about pivot point 20. By including the switchback segments 24/29 and 30/25, the maximum width B of instrument 10 over its midsection 13 is about the same (typically only slightly larger) than the maximum width A of the instrument over midsection 13 when in its closed position as shown in FIG. 1. This aspect of the invention allows instrument 10 to be worked by a surgeon without any significant change in the width of the instrument over its midsection 13, which constitutes a substantial portion of the length of the overall instrument. Because the switchback segments 24/29 and 30/25 are located entirely on opposite sides of centerline 16, the cross sectional width C of the instrument in these regions actually decreases when the instrument is moved from its closed position as shown in FIG. 1 toward its spread position as shown in FIG. 2.

For comparison purposes the outline of a corresponding surgical hand instrument 10' for open surgery is shown in shadow. As can be seen, the prior art instrument 10' is different from instrument 10 of the present invention in that it includes no switchback segments. In other words, handle 14, surgical tip 12 and the instrument's length are substantially identical for the prior art instrument 10' and the instrument 10 according to the present invention. Rather than having switchback segments 24, 29, 25 and 30 as in the present invention, the counterpart instrument 10' includes relatively straight connection segments 29', 24', 25' and 30'. The result of this configuration is that the maximum width B of instrument 10 over midsection 13 is substantially smaller than a maximum width W over an equivalent midsection of the corresponding scissor action hand instrument 10' for open surgery. In other words, instrument 10 includes a substantial length L in midsection 13 in which the width of the instrument remains about the same when moving from a closed position toward a spread position, whereas the prior art instrument 10' includes a relatively short portion of its length L' in which the width remains about the same when the instrument is moved from a closed position toward a spread position. If the switchback segments are made sufficiently long, length L can typically be at least double the length of L' for a given pair of corresponding instruments.

Although the present invention has been illustrated in FIGS. 1 and 2 as a pair of Foerster sponge forceps having proximal and distal switchback segments according to the present invention, the low profile concepts of the present invention can be applied to virtually any scissor action hand instrument for open surgery. Since most surgeons originally learned and have come accustomed to practicing a given surgical procedure in an open or invasive way, they have likewise come accustomed to the feel and behavior of the corresponding scissor action surgical hand instruments for open surgery used in these procedures. For purposes of the present invention, a corresponding scissor action surgical hand instrument is one shown in any catalog of surgical hand instruments available to healthcare providers and others skilled in the art. So that the surgical hand instruments according to the present invention feel and behave like their counterpart instruments for open surgery, the present invention preferably has a combination of features rendering it substantially similar to a corresponding scissor action hand instrument for open surgery. In particular, instruments according to the present invention preferably have a combination surgical tip, length, weight, balance, relative motion ratio of the handle to the surgical tip and tactile shape of the handle substantially similar to a corresponding instrument for open surgery. This combination of features should be so substantially similar that a surgeon who is unable to see the middle section of the instrument would be unable to determine whether the instrument was the present invention or a corresponding instrument for open surgery. In order to make the hand instruments according to the present invention even more like their open surgery counterparts, the first handle portion 28, second handle portion 23, first surgical tip portion 26, second surgical tip portion 21 and the length of the instrument along centerline 16 are substantially identical to corresponding portions of a scissor action hand instrument 10' for open surgery. By properly machining and using appropriate amounts of material in the switchback segments, instruments according to the present invention can be made to also have a weight and balance that is substantially identical to a corresponding scissor action hand instrument for open surgery. With all of these similarities, physicians are much more likely to adopt a set of low profile instruments according to the present invention so that they will be able to use the same instruments for a given surgical procedure whether it be performed in an open invasive way or by using the less invasive technique of entering the body through a small incision opening.

Figure 3:
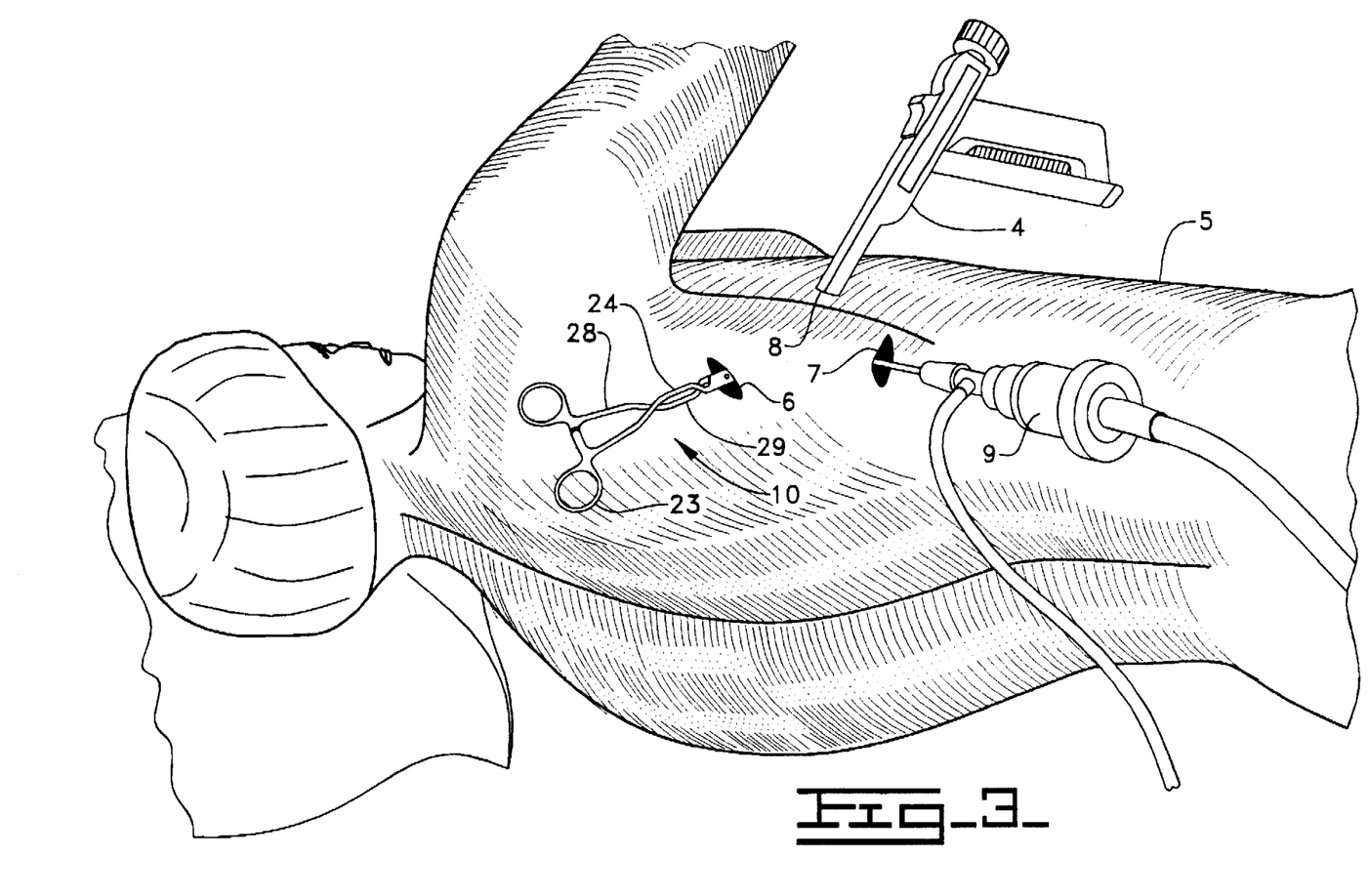
FIG. 3 is a perspective view of a person undergoing a less invasive surgical procedure utilizing the low profile surgical hand instrument shown in FIGS. 1 and 2.

Referring now to FIG. 3, Foerster sponge forceps 10 illustrated in FIGS. 1 and 2 are shown protruding from the upper torso of a patient 5 through a relatively small incision opening 6. The patient is shown undergoing a lobectomy surgical procedure in a less invasive manner. As is known in the art, the surgeon views the area undergoing the surgical procedure via a camera 9 protruding through a second small incision 7. While viewing the area on a view screen, the surgeon manipulates instrument 10 and a second instrument 4, which penetrates patient 5 through a third small incision 8. Hand instrument 10 includes a relatively long length of its midsection in which the maximum width remains relatively small when the instrument is spread. This allows a surgeon to use one set of instruments regardless of the size and shape of the patient and how much tissue depth exists between the incision 6 and the area undergoing the operation. Also the low profile features of the present invention allow the tissue to be approached directly by moving the instrument for and aft along its centerline. This is far more desirable than the necessity to approach the same tissue from the side if using a counterpart rotary action surgical hand instrument. This aspect of many rotary action surgical hand instruments that must normally be used in these less invasive surgical techniques is very undesirable since not only does the instrument feel and behave differently but must also be used in a different manner from the corresponding scissor action surgical hand instrument for open surgery. The direct approach allowed by the low profile instruments of the present invention also allows the incision into the patient's body to be placed at a more desirable location.

Figure 4:
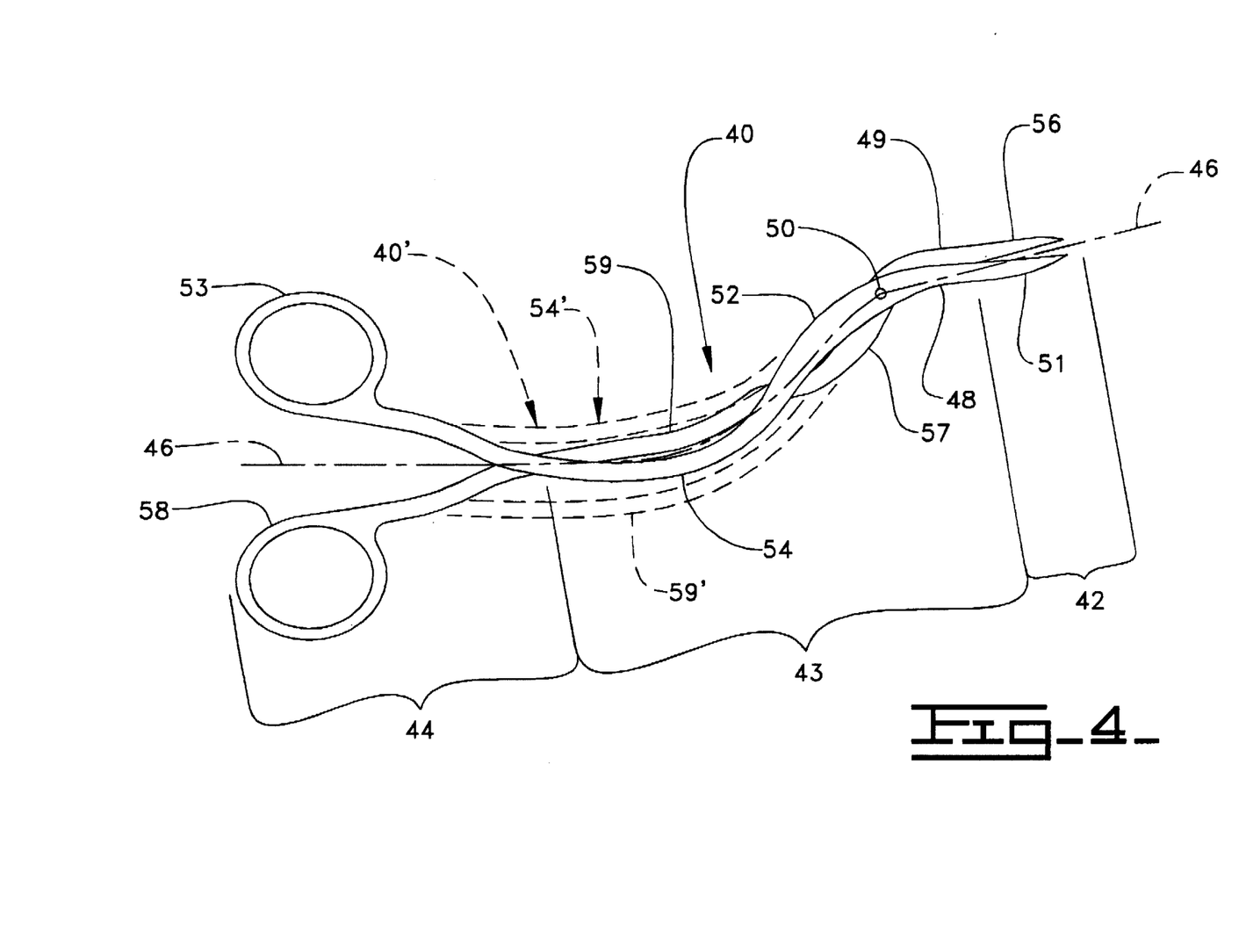
FIG. 4 is a front elevational view of a low profile surgical hand instrument according to another embodiment of the present invention having a curved centerline.

Referring now to FIG. 4, a pair of DeBakey S-Shaped scissors 40 include switchback segments 54 and 59 according to the present invention. Instrument 40 includes a surgical tip portion 42 separated from a handle portion 44 by a middle section 43 that contains the switchback segments. The instrument is made up of a first member 48 and second member 49, both formed from a single solid piece of a suitable surgical metallic alloy. The members are pinned to one another at pivot point 50.

First member 48 includes a scissor blade 51 separated from handle portion 53 by a middle portion 52. The second member 49 includes a scissor blade 56 separated from a handle portion 58 by a middle portion 57. A curved centerline 46 that passes through pivot point 50 separates blades 51 and 56 as well as handle portions 53 and 58. Middle portions 52 and 57 include a pair of switchback segments 54 and 59, respectively that lie on an opposite side of centerline 46 from their connected handle portions. In this case, only one set of switchback segments are utilized, and the segments are located proximally of the pivot point 50. For comparison purposes, the relatively large profile segments 54' and 59' for a corresponding hand instrument 40' for open surgery are illustrated. The low profile features of the present invention allow scissors 42 to be used with a less invasive surgical procedure whereas the corresponding scissors 40' are really suitable only for use in open surgical techniques.

Figure 5:
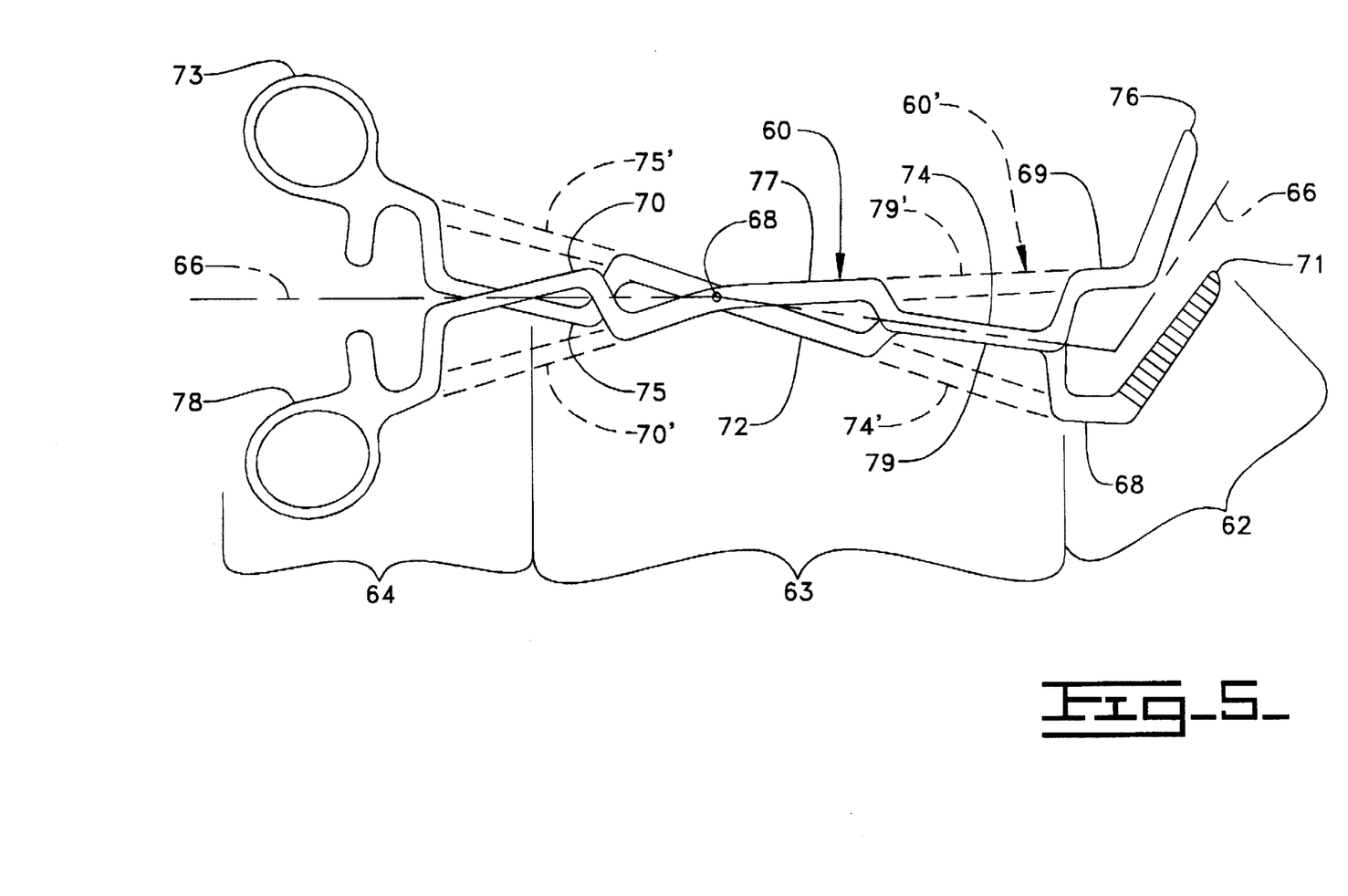
FIG. 5 is an isometric view of a low profile surgical hand instrument according to still another embodiment of the present invention.

Referring now to FIG. 5, a Glassman anterior resection clamp 60 having low profile features according to the present invention is illustrated. Those familiar with such an instrument will recognize that centerline 66 in this case appears to have a zigzag shape when viewed from the side. Nevertheless, instrument 60 is like other examples of the present invention in that it includes a surgical tip (clamp) 62 separated from a handle 64 by a middle section 63, which contains low profile switchback segments. Like all embodiments of the present invention a first member 68 is pinned to a second member 69 at a pivot point 61 located in the respective middle portions 72 and 77 of the members. First member 68 includes a surgical tip portion 71 separated from a handle portion 73 by a middle portion 72. Likewise, second member 69 includes a surgical tip portion 76 separated from a handle portion 78 by a middle portion 77. Middle portion 72 includes a distal switchback segment 74 and a proximal switchback segment 75, and middle portion 77 includes adjacent switchback segments 79 and 70, respectively. For comparison purposes, a corresponding resection clamp 60' includes relatively direct connection segments 79', 74', 75' and 70', which give the prior art instrument a relatively large profile in middle section 63 when spread as shown.

Figure 6:
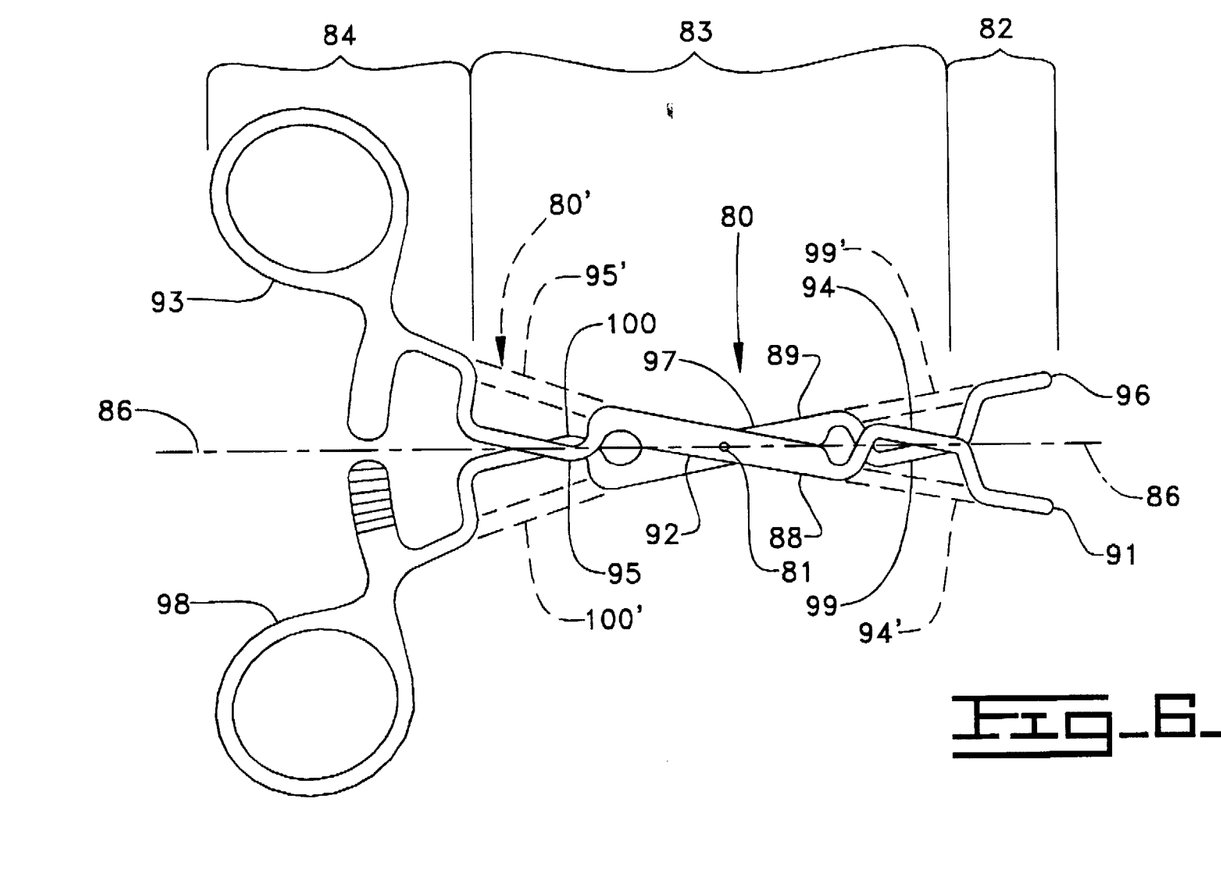
FIG. 6 is a front elevational view of a low profile surgical hand instrument according to another embodiment of the present invention.
Figure 7:
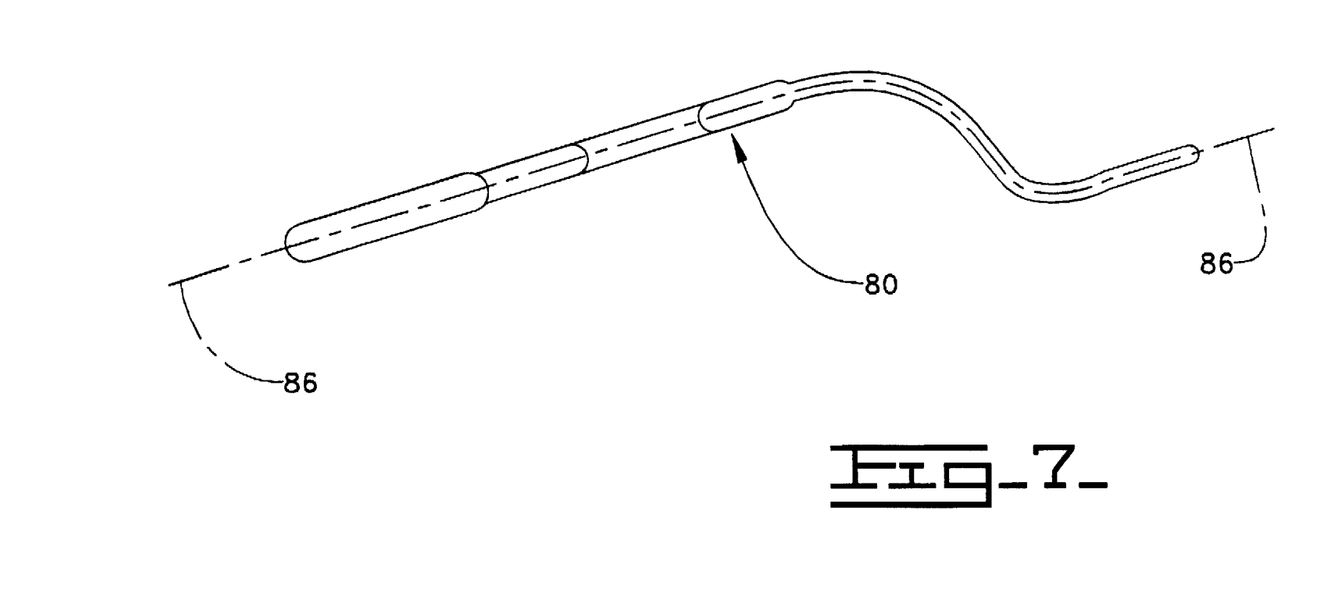
FIG. 7 is a side elevational view of the low profile surgical hand instrument shown in FIG. 6.

Referring now to FIGS. 6 and 7 still another example instrument 80 having the low profile switchback features of the present invention is illustrated. In this example embodiment instrument 80 is a Gregory external carotid clamp which has a clamp tip 82 separated from a handle 84 by a low profile middle section 83. FIG. 7 shows that the centerline of instrument 80 includes a relatively extreme curvature. First member 88 includes clamp tip 91 separated from handle portion 93 by a middle portion 92. Second member 89, which is attached to the first member 88 at pivot point 81, includes a clamp tip 96 separated from a handle portion 98 by middle portion 97. Middle portion 92 includes a distal switchback segment 94 and proximal switchback segment 95. Likewise, middle portion 97 includes adjacent distal switchback segment 99 and proximal switchback segment 100. The switchback segments lie entirely on opposite sides of centerline 86 when the instrument is in a closed position. Again, for comparison purposes, a prior art corresponding instrument 80' includes relatively direct connection segments 99', 94', 95' and 100', which give it a relatively large profile in midsection 83 when spread open as shown.

Those skilled in the art will appreciate that the embodiments of the present invention illustrated in FIGS. 4–7 are included only to show that the low profile switchback segment concepts of the present invention can be applied to virtually any scissor action hand instrument for open surgery, even those having curved or zigzag centerlines. Nevertheless, the present invention probably finds its best application in planar type straight instruments of the type illustrated in FIGS. 1 and 2, primarily because such instruments can be utilized through a small incision and approach a surgical area directly along a straight line. Those skilled in the art will appreciate that the depth and length of the switchback segments should be chosen such that when the instrument is at its maximum normal spread, a relatively long portion of the midsection length retains a relatively small maximum width relative to a corresponding scissor action hand instrument for open surgery. Although the low profile switchback concepts of the present invention can be applied to existing scissor action hand instruments for open surgery, there is no reason why these low profile concepts can not also be applied to scissor action hand instruments having surgical tips not yet known in the art.

The above examples should be viewed as illustrative examples only, and are not intended to limit the scope of the present invention in any way. The scope of the present invention is intended to be defined solely in terms of the claims set forth below.

I claim:

1. A scissor action low profile surgical hand instrument comprising:

a first member formed from a single piece of a surgical metallic alloy into a first handle portion separated from a first surgical tip portion by a first middle portion;

a second member formed from a single piece of a surgical metallic alloy into a second handle portion separated from a second surgical tip portion by a second middle portion;

said first middle portion being pivotably attached to said second middle portion at a pivot point;

a centerline passing through said pivot point separates said first handle portion from said second handle portion and said first surgical tip portion from said second surgical tip portion;

said first middle portion including a first switchback segment positioned at least partially on an opposite side of said centerline from one of either said first handle portion or said first surgical tip portion;

said second middle portion including a second switchback segment positioned at least partially on an opposite side of said centerline from one of either said second handle portion or said second surgical tip portion at a location adjacent said first switchback segment of said first middle portion; and whereby said first member is pivotable with respect to said second member from a closed position toward a spread position independently of said first switchback segment and said second switchback segment.

2. The surgical hand instrument of claim 1 wherein said first switchback segment is positioned distally of said pivot point and at least partially on an opposite side of said centerline from said first surgical tip portion; and said second switchback segment is positioned at least partially on an opposite side of said centerline from said second surgical tip portion at a location adjacent said first distal switchback segment.

3. The surgical hand instrument of claim 2 wherein said first middle portion has a first proximal switchback segment positioned proximally of said pivot point and at least partially on an opposite side of said centerline from said first handle portion and; and said second middle portion has a second proximal switchback segment positioned at least partially on an opposite side of said centerline from said second handle portion at a location adjacent said first proximal switchback segment of said first middle portion.

4. The surgical hand instrument of claim 3 wherein said first switchback segment is positioned entirely on an opposite side of said centerline from said second switchback segment.

5. The surgical hand instrument of claim 4 wherein said first proximal switchback segment is positioned entirely on an opposite side of said centerline from said second proximal switchback segment.

6. The surgical hand instrument of claim 1 wherein said instrument has a closed maximum width in said midsection when in said closed position that is about the same as a maximum width of said midsection when in a partially spread position.

7. A scissor action low profile surgical hand instrument comprising:

a first member having a first handle portion separated from a first surgical tip portion by a first middle portion;

a second member having a second handle portion separated from a second surgical tip portion by a second middle portion;

said first middle portion being pivotably attached to said second middle portion at a pivot point;

a centerline passing through said pivot point separates said first handle portion from said second handle portion and said first surgical tip portion from said second surgical tip portion;

said first middle portion having a first distal switchback segment positioned distally of said pivot point and at least partially on an opposite side of said centerline from said first surgical tip portion;

said second middle portion having a second distal switchback segment positioned at least partially on an opposite side of said centerline from said second surgical tip portion at a location adjacent said first distal switchback segment; and whereby said instrument has a closed maximum width across said first middle portion and said second middle portion when in a closed position that is about the same as a spread maximum width across said first middle portions and said second middle portion when in a partially spread position.

8. The surgical hand instrument of claim 7 wherein said first middle portion has a first proximal switchback segment positioned proximally of said pivot point and at least partially on an opposite side of said centerline from said first handle portion and; and said second middle portion has a second proximal switchback segment positioned at least partially on an opposite side of said centerline from said second handle portion at a location adjacent said first proximal switchback segment of said first middle portion.

9. The surgical hand instrument of claim 8 wherein said first distal switchback segment is positioned entirely on an opposite side of said centerline from said second distal switchback segment.

10. The surgical hand instrument of claim 9 wherein said first proximal switchback segment is positioned entirely on an opposite side of said centerline from said second proximal switchback segment.

11. The surgical hand instrument of claim 10 wherein the instrument has a closed maximum width in said midsection when in said closed position that is about the same as a maximum width of said midsection when in a partially spread position.

12. A scissor action low profile surgical hand instrument consisting essentially of:

a first solid member formed from a single piece of a surgical metallic alloy into having a first handle portion separated from a first surgical tip portion by a first middle portion;

a second solid member formed from a single piece of a surgical metallic alloy into having a second handle portion separated from a second surgical tip portion by a second middle portion;

said first middle portion being pivotably attached to said second middle portion at a single pivot point;

a centerline passing through said pivot point separates said first handle portion from said second handle portion and said first surgical tip portion from said second surgical tip portion;

said first middle portion having a first distal switchback segment positioned distally of said pivot point and entirely on an opposite side of said centerline from said first surgical tip portion;

said second middle portion having a second distal switchback segment positioned entirely on an opposite side of said centerline from said second surgical tip portion at a location adjacent said first midswitchback segment;

said first middle portion has a first proximal switchback segment positioned proximally of said pivot point and entirely on an opposite side of said centerline from said first handle portion;

said second middle portion has a second proximal switchback segment positioned entirely on an opposite side of said centerline from said second handle portion at a location adjacent said first proximal switchback segment of said first middle portion; and the instrument having a width across said proximal switchback segments and a width across said distal switchback segments that decrease when the instrument is moved from a closed position toward a spread position.

13. The surgical hand instrument of claim 12 wherein the instrument has a closed maximum width in said midsection when in said closed position that is about the same as a maximum width of said midsection when in a partially spread position.

14. The surgical hand instrument of claim 12 having a closed maximum width of a midsection when in said closed position that is about the same as a spread maximum width when in a partially spread position.

* * * * *